United States Patent [19]

Giesecke et al.

[11] 4,429,135
[45] Jan. 31, 1984

[54] PROCESS FOR THE PRODUCTION OF 1,2,4-TRIAZOLIDINE-3,5-DIONES MONOSUBSTITUTED IN THE 4-POSITION

[75] Inventors: Henning Giesecke, Cologne; Rudolf Merten, Leverkusen; Ludwig Rottmaier, Odenthal, all of Fed. Rep. of Germany

[73] Assignee: Bayer Aktiengesellschaft, Leverkusen, Fed. Rep. of Germany

[21] Appl. No.: 278,654

[22] Filed: Jun. 29, 1981

[30] Foreign Application Priority Data

Jul. 21, 1980 [DE] Fed. Rep. of Germany ....... 3027612

[51] Int. Cl.³ .......................................... C07D 249/12
[52] U.S. Cl. .................................................. 548/264
[58] Field of Search ........................................ 548/264

[56] References Cited

U.S. PATENT DOCUMENTS 3,636,000 1/1972 Spitulnik ............................ 548/264
4,323,687 4/1982 Merten et al. ...................... 548/264

FOREIGN PATENT DOCUMENTS 792243 8/1968 Canada ................................ 548/264
1447532 6/1966 France .
1470310 1/1967 France .
2061024 6/1971 France .

OTHER PUBLICATIONS

Temple, Jr.; Triazoles 1,2,4 Heterocyclic Compounds pp. 526-527 (1981).
Justus Liebig's Annalen der Chemie; vol. 283, pp. 41-48 (1894).
Chemical Abstracts, vol. 67, No. 25, p. 11009, item 116858y (Dec. 18, 1967).
Canadian Journal of Chemistry, vol. 50, No. 11, pp. 2661-2666 (1972).

*Primary Examiner*—Mary C. Lee
*Attorney, Agent, or Firm*—Connolly and Hutz

[57] ABSTRACT

A process for the production of 1,2,4-triazolidine-3,5-diones corresponding to the general formula I

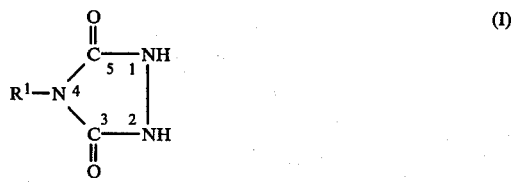

in which $R^1$ represents a monofunctional, optionally substituted hydrocarbon radical, optionally interrupted by hetero atoms or hetero atomic groups, characterized in that hydrazodicarbonamide or 1,2,4-triazolidine-3,5-dione is reacted with a primary amine corresponding to the general formula II

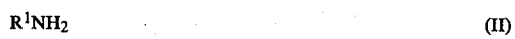

or a monofunctional hydrazodiacarbonamide corresponding to the formula III

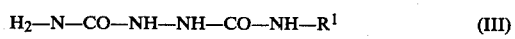

in which $R^1$ is as defined for formula I, at a temperature in the range from 150° to 280° C., under pressure of from 50 mbars to 5 bars, the reaction being accompanied by the elimination of ammonia.

4 Claims, No Drawings

PROCESS FOR THE PRODUCTION OF 1,2,4-TRIAZOLIDINE-3,5-DIONES MONOSUBSTITUTED IN THE 4-POSITION

This invention relates to a process for the production of 1,2,4-triazolidine-3,5-diones substituted in the 4-position by optionally substituted hydrocarbon radicals which may be interrupted by heteroatoms or hetero atomic groups.

The production of 4-phenyl-1,2,4-triazolidine-3,5-dione from hydrazodicarbonamide and aniline hydrochloride is known. According to Liebigs Ann. 283, 41 (1894), the production is carried out by heating a mixture of hydrazodicarbonamide and aniline hydrochloride in the melt. However, this method is unsuitable for working on an industrial scale. The melt obtained is heavily contaminated and, after cooling, accumulates in the form of a solid, hard mass which has to be size-reduced and purified. 4-phenyl-1,2,4-triazolidine-3,5-dione is formed only as a secondary product.

Another method of production 1,2,4-triazolidine-3,5-diones substituted in the 4-position is to cyclise 1-alkoxy carbonyl-4-phenyl (or -4-n-butyl)-semicarbazides, as described in Archiv der Pharmazie 294, 370 (1961). The yields of the desired end product vary from 80 to 95%. However, this process has never been successfully worked on an industrial scale on account of the high price of the starting compounds and the sensitivity of hydrolysis of the intermediate products.

The present invention provides a process for the production of 1,2,4-triazolidine-3,5-diones corresponding to the following general formula (I);

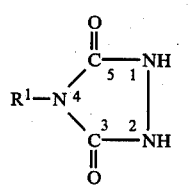
(I)

in which $R^1$ represents a monofunctional, unsubstituted or substituted, linear or branched aliphatic $C_1$–$C_{30}$, preferably $C_5$–$C_{19}$ radical, a monofunctional, unsubstituted or substituted cycloaliphatic $C_5$–$C_{21}$ radical, a monofunctional, unsubstituted or substituted aliphatic-aromatic $C_7$–$C_{17}$, preferably $C_7$–$C_{10}$ radical or a monofunctional, unsubstituted or substituted aromatic $C_6$–$C_{21}$, preferably $C_6$–$C_{15}$, radical, the aliphatic radicals mentioned above optionally being interrupted by one or more oxygen atoms or tertiary nitrogen atoms and the polynuclear aliphatic-aromatic, polynuclear cycloaliphatic and polynuclear aromatic radicals mentioned above optionally being interrupted by at least one alkylene group containing from 1 to 4 carbon atoms, by at least one oxygen atom or tertiary nitrogen atom or by at least one sulfonyl group

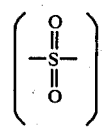

characterised in that hydrazodicarbonamide or 1,2,4-triazolidine-3,5-dione is reacted with a primary amine corresponding to the following formula $$R^1—NH_2 \qquad (II)$$

in which $R^1$ is as just defined,
in the presence or absence of a solvent or solvent mixture, at temperatures in the range from 150° to 280° C., under pressures of from 50 mbar to 5 bar and optionally in the presence of an acid or basic catalyst, the reaction being accompanied by the elimination of ammonia.

According to a modification of the foregoing described process the same compounds corresponding to formula I may also be obtained by heating a monosubstituted hydrazodicarbon-amide corresponding to the following formula III $$H_2N—CO—NH—NH—CO—NH—R^1 \qquad (III)$$

in which $R^1$ has the same meaning as in formula 1, under the same conditions as described above instead of reacting together the starting materials hydrazodicarbonamide and a primary amine or 1,2,4-triazolidine-3,5-dione and a primary amine.

Preferred substituents for $R^1$ are alkoxy carbonyl groups preferably containing from 1 to 4 carbon atoms in the alkoxy groups, CN, $NO_2$, alkyl mercapto groups containing from 1 to 4 carbons in the alkyl group, dialkyl amino groups preferably containing from 1 to 6 carbon atoms in each alkyl group, halogens (preferably fluorine, chlorine and bromine) and, in the case of the aromatic radicals, lower alkyl groups preferably containing from 1 to 4 carbon atoms in addition to the substituents mentioned above.

Compounds of formula (1) in which the radical $R^1$ is unsubstituted are particularly preferred.

Preferred radicals $R^1$ correspond for example to the following formulae:

$$CH_3—(CH_2)_m— \quad m = 0\text{–}17 \qquad 1.$$

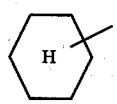   2.

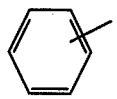   3.

   4.

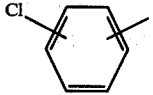   5.

$$C_4H_9—O—(CH_2)_3— \qquad 6.$$

7. 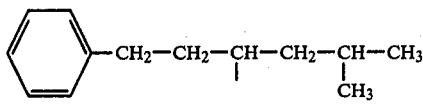

8. 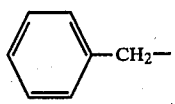

It is preferred to use from 0.9 to 1.1 moles of hydrazodicarbonamide or from 0.9 to 1.1 moles of 1,2,4-triazolidine-3,5-dione per mole of the amine corresponding to formula II.

The hydrazodicarbonamide used for the reaction with the primary amine corresponding to formula II is known from the literature and is obtained in a substantially quantitative yield in the reaction of 1 mole of hydrazine with 2 moles of urea in aqueous medium with elimination of ammonia. The hydrazodicarbonamide which accumulates as a deposit is isolated by filtration under suction and may be immediately further processed as a filter-moist product providing the residual water can be removed during the cyclisation reaction. Dried hydrazodicarbonamide may, of course, also be used for further processing. It is also possible, following the addition of a suitable solvent to the resulting suspension of hydrazodicarbonamide in water, to distill off the water by heating and to react the residual hydrazodicarbonamide with amines to form the triazolidine-3,5-diones mentioned above.

According to the modification the N-monosubstituted hydrazodicarbonamides of formula III used for producing the compounds of formula I are obtained by reacting semicarbazide with isocyanates corresponding to the following formula:

$$R^1-NCO \quad (IV)$$

in which $R^1$ has the same meaning as in formula (I).

In general, it is best to carry out the reaction of the semicarbazide and isocyanate to form the mono-substituted hydrazodicarbonamides corresponding to formula (III) in a solvent or diluent, in which case the starting materials, in substantially equivalent quantitative ratios (1 mole of semicarbazide=1 OCN-group), may either be dissolved or only suspended. It is of course also possible to carry out the reaction in the absence of a solvent or diluent. Suitable solvents for the process are, for example, aromatic hydrocarbons, chlorinated aromatic hydrocarbons, benzonitrile, aliphatic hydrocarbons, esters and ketones. Particularly suitable solvents are toluene, xylene, mesitylene, chlorobenzene, dichlorobenzene, N-methyl pyrrolidone, dimethyl formamide, dimethyl acetamide, hexamethyl phosphoric acid triamide, tetramethyl urea, nitromethane and nitrobenzene. However, it is also possible to carry out the reaction at lower temperatures in water or lower alcohols.

The reaction may be carried out at temperatures of from −30° to +150° C. It is preferred to work at temperatures in the range from −20° to +100° C. and particularly preferred to work at temperatures in the range from −10° to +80° C.

The reaction mechanisms by which each of the three embodiments of the process according to the invention takes place are immaterial. All three variants lead simply, smoothly and reproducibly to high yields of the compounds corresponding to formula (1).

It is possible, even probable, that, in the reaction of the hydrazodicarbonamide with the primary amine accompanied by the elimination of ammonia or in the reaction of the 1,2,4-triazolidine-3,5-dione with the primary amine accompanied by ring opening, monosubstituted hydrazodicarbonamide corresponding to formula III is initially formed, the compounds of formula I being obtained therefrom through cyclisation with elimination of ammonia.

In all three embodiments of the process, the reaction temperature is generally in the range from 150° to 280° C., preferably in the range from 170° to 250° C. and, more particularly, in the range 175° to 220° C. The higher the temperature, the faster the reaction, although the danger of undesirable secondary products being formed and decomposition of the solvent increase.

The reaction times are generally in the range from 1 to 40 hours, although they may even be longer or shorter in exceptional cases.

To accelerate the reaction, it may be advisable to add acid or basic catalysts. Metal alcoholates (for example sodium methylate and tin (II)octoate) and tertiary amines are particularly suitable.

The reaction pressure is normally in the range from 50 mbars to 5 bars. If the reaction is carried out at a pressure higher than atmospheric pressure, the ammonia formed has to be periodically removed so that the cyclisation reaction is preferably carried out under a pressure of from 300 mbars to 2 bars.

It can be advantageous to keep the concentration of ammonia eliminated in the reaction vessel at a low level. This can be done by any known method, for example by blowing with an inert gas, such as air, nitrogen, carbon dioxide or steam. Low-boiling solvents, for example aliphatic, aromatic, araliphatic hydrocarbons, their commercial mixtures and chlorinated hydrocarbons preferably containing from 1 to 10 hydrocarbon atoms, such as cyclohexane, toluene, xylenes, petroleum ether or chloroform, which are pumped or introduced dropwise into the reactor in liquid form, may also be used for removing the ammonia. The partial pressure of the ammonia may also be reduced by filtration under suction, i.e. by applying sub-atmospheric pressure.

The organic solvents used in the reaction should show adequate thermal stability under the reaction conditions and should be chemically inert to hydrazodicarbonamides and triazolidine-3,5-diones. In addition, the boiling point of the solvent used should be sufficiently high to ensure that the solvent does not distill off during the reaction.

The boiling points of the solvents at atmospheric pressure generally amount to at least 150° C. and preferably to between about 175° and 280° C. The solvents may be miscible, partly miscible or immiscible with water at room temperature.

Suitable solvents are (A) nitrogen-containing solvents N-substituted by phenyl or $C_1$-$C_8$-alkyl groups, for example N-substituted pyrrolidones, urethanes, cyclic urethanes or ureas, for example N-methyl pyrrolidone, ethyl phenyl urethane, 5-methyl-2-oxazolidinone, tetramethyl urea; also polyethers, for example diethylene glycol diethyl ether; phenols, such as cresols, halogen-substituted phenols and cresols, for example 4-chlorophenyl: dialkyl sulfones and cyclic sulfones each containing at most 12 carbon atoms, for example dimethyl sulfone or sulfolan; aromatic or araliphatic ethers, such as diphenyl ether and dibenzyl ether, high-boiling alcohols, for example ethylene glycol. Other suitable solvents are (B) aliphatic, cycloaliphatic, aromatic and araliphatic hydrocarbons and their commercial mixtures, for example, dodecane, decalin, trimethyl benzene, naphthalene, 1-methyl naphthalene, diphenyl methane, halogenated aliphatic, cycloaliphatic, aromatic and araliphatic hydrocarbons and their commercial mixtures, such as dodecyl chloride, 1,2,3-trichloro-benzene, 1-chloronaphthalene and dichlorotoluene.

It is particularly preferred to use diphenyl ether, diphenyl methane, 1-methyl naphthalene, dialkyl sulfones and cyclic sulfones, particularly sulfolan, and N-methyl pyrrolidone.

The reaction mixtures with the polar solvents mentioned above in (A) obtained after cyclisation (reaction) may be mixed during cooling with solvents inert to triazolidine-3,5-diones such as aliphatic, cycloaliphatic, araliphatic or aromatic hydrocarbons, for example cyclohexane, toluene, xylene, aliphatic or cycloaliphatic alcohols, for example butanol, cyclohexanol and ethers of esters derived therefrom, for example glycol monomethyl ether, butyl acetate, ketones, for example acetone or ethyl methyl ketone, and, where water-miscible polar solvents are used, even with water, so that the triazolidine-3,5-diones which crystallise out are obtained in relatively high yields and in relatively pure form. The additions may amount to as much as 500% by weight, based on the polar solvent.

The process according to the invention is suitable both for batch working and also for continuous working. Where the process is carried out continuously, cyclisation is carried out in known manner, for example in cascades or in tube reactors. The batch variant is preferred.

The fact that the reaction takes place smoothly in the processes described above was surprising because the cyclisation of hydrazodicarbonamide in the presence of primary amines has been expected to give poorly separable mixtures of 1,2,4-triazolidine-3,5-diones corresponding to formula I.

It was also surprising to find that the 1,2,4-triazolidine-3,5-dione reacts with primary amines to form 4-substituted triazolidine-3,5-diones although it is characterised by considerable thermal resistance.

The 1,2,4-triazolidine-3,5-diones corresponding to formula (I) are valuable starting materials for the production of temperature-resistant polymers. Dihydroxyl alkl triazolidine-3,5-diones produced therefrom are used, for example, as crosslinking components in temperature-resistant electrical insulating lacquers, whereas corresponding diglycidyl triazolidine-3,5-diones are used, for example, as crosslinkers in powder lacquers applied by electrostatic powder spraying. In addition, 1,2,4-triazolidine-3,5-diones corresponding to formula (I) may be used in photographic compositions.

The percentages quoted in the following Examples represent percentages by weight.

EXAMPLE 1

60 g of hydrazodicarbonamide and 56 g of n-hexylamine are stirred in 100 ml of N-methy pyrrolidone for 6 hours at 150° C., for 20 hours at 175° C. and for 20 hours at 180° C. The solvent is then distilled off in vacuo and the residue is triturated with 100 ml of 10% sodium hydroxide solution. The deposit is isolated by filtration under suction and the filtrate is neutralised with 10% hydrochloric acid. A deposit is precipitated and is isolated by filtration under suction, washed with water and dried in vacuo, giving 75 g (81% of the theoretical yield) of 4-(n-hexyl)-1,2,4-triazolidine-3,5-dione in the form of colourless crystals melting at 144° C. to 145° C.

|  |  | C | H | N |
|---|---|---|---|---|
| $C_8H_{15}N_3O_2$ | calculated | 51.87% | 8.16% | 22.69% |
| (185.2) | observed | 51.9% | 8.4% | 22.6% |

MS (m/e): mol. peak 175

EXAMPLE 2

10.1 g of triazolidine-3,5-dione and 10 g of cyclohexylamine are stirred in 20 ml of N-methyl pyrrolidone for 4 hours at 175° C. and for 8 hours at 180° C. The solvent is then distilled off in vacuo, the residue is triturated with 10 ml of a 10% sodium hydroxide solution and the deposit is isolated by filtration under suction. The filtrate is neutralised with 10% HCl. A deposit is precipitated which is isolated by filtration under suction and washed with water, giving 6.6 g (35% of the theoretical yield) of 4-cyclohexyl-1,2,4-triazolidine-3,5-dione in the form of colourless crystals melting at 240° to 245° C.

|  |  | C | H | N |
|---|---|---|---|---|
| $C_8H_{13}N_3O_2$ | calculated | 52.45% | 7.15% | 22.94% |
| (183.2) | observed | 52.5% | 7.2% | 22.7% |

EXAMPLE 3

53.5 g of benzylamine and 59 g of hydrazodicarbonamide are stirred in 100 ml of N-methyl pyrrolidone for 4 hours at 175° C. and for 5 hours at 200° C. The solvent is then distilled off in vacuo, the residue is triturated with 50 ml of a 10% sodium hydroxide solution and the residue is isolated by filtration under suction. The filtrate is neutralised with 10% hydrochloric acid. A deposit is formed which is filtered off under suction and washed with water, giving 67 g (70% of the theoretical yield) of 4-benzyl-1,2,4-triazolidine-3,5-dione in the form of colourless crystals melting at 185° to 188° C. (CH₃CN).

|  |  | C | H | N |
|---|---|---|---|---|
| $C_9H_9N_3O_2$ | calculated | 56.54% | 4.74% | 21.98% |
| (191.2) | observed | 56.8% | 4.7% | 22.2% |

$^1$H-NMR (d-DMSO):=5.60 (s; 2H), 7.33 (s; 5H$_{arom.}$) 10.1 ppm (wide; 2H).

IR (KBr): 1776, 1674 cm$^{-1}$ (C=O).

EXAMPLE 4

118 g of hydrazodicarbonamide and 100 g of cyclohexyl amine are stirred in 100 ml of N-methyl pyrrolidone for 2 hours at 160° C., for 7 hours at 175° C. and for 10 hours at 200° C. The solvent is then distilled off in vacuo and the residue is triturated with 100 ml of a 10% sodium hydroxide solution. The deposit is isolated by filtration under suction and the filtrate is neutralised with 10% hydrochloric acid. A deposit is precipitated and is isolated by filtration under suction, washed with water and dried in vacuo, giving 132 g (76% of the theoretical yield) of 4-cyclohexyl-1,2,4-triazolidine-3,5-dione (identical with the compounds produced in accordance with Example 2).

EXAMPLE 5

360 g of hydrazodicarbonamide, 807 g of stearylamine and 1 ml of tin(II)dioctoate are stirred in 1 liter of N-methyl pyrrolidone for 4 hours at 175° C. and for 6 hours at 200° C. A deposit is precipitated on cooling and is filtered off under suction and washed with water, giving 955 g (90% of the theoretical yield) of 4-stearyl-1,2,4-triazolidine-3,5-dione in the form of colourless crystals melting at 118° to 120° C.

|  |  | C | H | N |
|---|---|---|---|---|
| $C_{20}H_{39}N_3O_2$ | calculated | 67.94% | 11.12% | 11.89% |
| (353.6) | observed | 68.9% | 11.1% | 11,9% |

MS (m/e): mol. peak 353.

EXAMPLE 6

Soda is added in small portions to a solution of 111.5 g of semicarbazide hydrochloride in 700 g of water until there is no further evolution of gas.

A solution of 119 g of phenyl isocyanate in 100 g of acetone is then added dropwise at 40° C. To complete the reaction, the reaction mixture is stirred for 2 hours at 40° C. and the deposit formed is isolated by filtration under suction.

The deposit which is dried overnight in air is suspended in 300 g of sulfolan and the resulting suspension is heated to 250° C., the ammonia evolved being removed beyond 160° C. by applying a water jet vacuum of 420 mbars. After a reaction time of 5 hours, most of the solvent is removed under a pressure of 0.3 mbar and the residue left is recrystallised from n-butanol. Filtration under suction and drying give 134 g of 4-phenyl-1,2,4-triazolidine-3,5-dione melting at 202° to 203° C. (lit. 203° C.).

EXAMPLE 7

131 g of 3-butoxy propylamine and 120 g of hydrazodicarbonamide are stirred in 300 ml of N-methyl pyrrolidone for 1 hour at 150° C., for 2 hours at 175° C. and for 6 hours at 200° C. A deposit is precipitated on cooling which is isolated by filtration under suction and recrystallised from cyclohexane, giving 152 g (75% of the theoretical yield) of 4-(3-butoxypropyl)-1,2,4-triazolidine-3,5-dione in the form of colourless crystals melting at 83° to 85° C.

|  |  | C | H | N |
|---|---|---|---|---|
| $C_9H_{17}N_3O_3$ | calculated | 50.22% | 7.69% | 19.52% |
| (215,2) | observed | 50.2% | 8.1% | 19.8% |

$^1$H-NMR(CDCl$_3$=0.90 (t, 3H; J=6 Hz), 1.0–2.2 (m, 6H), 3.2–3.9 (m, 6H), 9.21 ppm (s, 2H).

EXAMPLE 8

191 g of 3-amino-5-methyl-1-phenyl hexane and 120 g of hydrazocarbonamide are stirred in 250 ml of N-methyl pyrrolidone for 1 hour at 150° C., for 1 hour at 175° C. and for 2 hours at 200° C. A deposit is precipitated on cooling and is isolated by filtration under suction and recrystallised from cyclohexane, giving 252 g (92% of the theoretical yield) of 4-(5-methyl-1-phenylhexyl-3(-1,2,4-triazolidine-3,5-dione in the form of colourless crystals melting at 114° to 115° C.

|  |  | C | H | N |
|---|---|---|---|---|
| $C_{15}H_{21}N_3O_3$ | calculated | 65.43% | 7.96% | 15.25% |
| (275.3) | observed | 65.2% | 7.4% | 14.4% |

IR (KBr): 1767, 1671 cm$^{-1}$ (C=O).

EXAMPLE 9

111.5 g of semicarbazide hydrochloride are dissolved in 250 ml of H$_2$O and the resulting solution neutralised with soda. 169 g of 1-naphthyl isocyanate in 100 ml of dioxane are then added dropwise with vigorous stirring and cooling at room temperature. The mixture is then stirred for another hour at room temperature. The deposit is isolated by filtration under suction and washed with H$_2$O.

The moist deposit is suspended in 1 liter of sulfolan and the resulting suspension stirred at 150° C. until no more H$_2$O distills off. The suspension is then stirred for 3 hours at 210° C./300 mbar. A deposit is formed on cooling which is isolated by filtration under suction and discarded. The mother liquor is concentrated in a high vacuum and the residue extracted with 300 ml of 10% sodium hydroxide solution. Acidification of the alkaline solution with hydrochloric acid produces a deposit which is isolated by filtration under suction and washed with water.

123 g (54% of the theoretical yield) of 4-naphthyl-1,2,4-triazolidine-3,5-dione are obtained in the form of colourless crystals melting at 283°–286° C.

|  |  | C | H | N |
|---|---|---|---|---|
| $C_{12}H_9N_3O_2$ | calculated | 63.43% | 3.99% | 18.50% |
| (227.2) | observed | 63.5% | 3.9% | 18.7% |

$^1$H-NMR(d$_7$-DMF)=7.4–8.2 (m, 7H arom). 10.43 ppm (s, 2H).

EXAMPLE 10

Soda is added in small portions to a solution of 111.5 g of semicarbazide hydrochloride in 1000 g of water until no more gas is evolved. A solution of 153.5 g of p-chlorophenyl isocyanate in 200 g of dioxane is then added dropwise at 35° to 40° C. To complete the reaction, the reaction mixture is stirred for 2 hours and the deposit is isolated by filtration under suction.

The deposit which is dried overnight in air is suspended in 500 g of N-methyl pyrrolidone and heated to 200° C., the ammonia evolved being removed beyond 160° C. by pressing over a stream of nitrogen. On completion of the reaction, the solvent is largely removed by applying a water jet vacuum, the residue left is dissolved in sodium hydroxide solution, the resulting alkaline solution is filtered off from insoluble constituents and adjusted to pH 2 with hydrochloric acid. Filtration under suction and drying gives 146 g of 4-(p-chlorophenyl)-1,2,4-triazolidine-3,5-dione melting at 234° to 236° C. (from ethanol), its structure being confirmed by IR- and NMR-spectra and by elemental analysis.

|  |  | C | H | Cl | N |
|---|---|---|---|---|---|
| $C_8H_6ClN_3O_2$ | calculated | 45.41% | 2.86% | 16.76% | 19.86% |

|   |   | C | H | Cl | N |
|---|---|---|---|---|---|
| (211.6) | observed | 45.4% | 2.8% | 16.9% | 19.7% |

EXAMPLE 11

111.5 g of semicarbazide hydrochloride are dissolved in 400 ml of water and the resulting solution neutralised with soda. 57 g of methyl isocyanate dissolved in 300 ml of dioxane are then added dropwise over a period of 1 hour with vigorous stirring at room temperature. After stirring for another 2 hours at room temperature, the deposit formed is isolated by filtration under suction. The deposit is then suspended in 1 liter of N-methyl pyrrolidone and the resulting solution is pyrrolysed for 10 hours at 200° C./300 mbars.

The solvent is then distilled off in vacuo and the residue is recrystallised from ethanol, giving 96 g (83% of the theoretical yield) of 4-methyl-1,2,4-triazolidine-3,5-dione in the form of colourless crystals melting at 230° to 232° C. (lit. 232°–233° C.).

APPLICATION EXAMPLE (a) 440 g of ethylene oxide are introduced over a period of 8 hours at 110° to 120° C. into 575 g of 4-methyl triazolidine-3,5-dione and 5 g of lithium chloride in 1000 g of dimethyl formamide in such a way that no ethylene oxide escapes. The solvent is distilled off by applying a vacuum. The residue is dissolved by heating in 1 liter of ethyl acetate. A deposit crystallises out on cooling and is isolated by filtration under suction and then dried.

1,2-bis-(2-hydroxyethyl)-4-methyl triazolidine-3,5-dione melting at 126°–127° C. (from ethanol) is obtained in a yield of 675 g. IR- and NMR-spectra in conjunction with elemental analysis confirm the assumed structure.

|   |   | C | H | N |
|---|---|---|---|---|
| $C_7H_{13}N_3O_4$ | calculated | 41.3% | 6.45% | 20.68% |
| (203.2) | observed | 41.5% | 6.2% | 20.6% |

(b) 291 g of terephthalic acid dimethyl ester, 203 g of 1,2-bis-(2-hydroxyethyl)-4-methyl triazolidine-3,5-dione from Example a, 31 g of 1,2-ethane diol and 92 g of glycerol are melted and 1 g of lead acetate, 0.5 g of titanium tetrabutylate and 50 ml of xylene are added to the resulting melt which is then heated for 8 hours to 200° C. The melt is then further heated to 200° C. over a period of 3 hours and condensation is continued for 4 hours by applying a vacuum. 547 g of a brown resin which is brittle at room temperature are obtained.

30 g of this resin are dissolved in 70 g of a commercial m-cresol, 0.9 g of a stabilised titanium tetrabutylate solution (prepared by heating 1 part by weight of a titanium tetrabutylate and 2 parts by weight of cresol) is added to the resulting solution which is then applied to a degreased glass plate and stoved for 20 minutes at 200° C. and for 10 minutes at 300° C. An elastic film having a smooth surface and a high softening temperature is obtained.

We claim:

1. A process for the production of a 1,2,4-triazolidine-3,5-dione of the formula

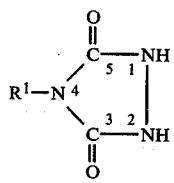

wherein $R^1$ is a monofunctional linear or branched aliphatic $C_1$–$C_{30}$ radical, a monofunctional cycloaliphatic $C_5$–$C_{21}$ radical, a monofunctional aliphatic-aromatic $C_7$–$C_{17}$ radical, a monofunctional aromatic $C_6$–$C_{21}$ radical, one of said radicals substituted by alkoxy carbonyl having from 1 to 4 carbon atoms in the alkoxy group, CN, $NO_2$, alkylmercapto having from 1 to 4 carbon atoms, dialkylamino having from 1 to 6 carbon atoms in each alkyl moiety or halogen, or one of said aromatic radicals substituted by alkyl having from 1 to 4 carbon atoms, said process comprising reacting 0.9 to 1.1 moles of hydrazodicarbonamide or 1,2,4-triazolidine-3,5-dione with one mole of a primary amine of the formula $$R^1NH_2$$

wherein $R^1$ is as aforesaid, at a temperature of from 150° to 280° C. and under a pressure of from 50 mbars to 5 bars in the presence of N-methyl pyrrolidone or sulfolan as solvent, said reaction being accompanied by the elimination of ammonia.

2. A modification of the process according to claim 1, wherein a monofunctional hydrazodicarbonamide of the formula $$H_2N-CO-NH-NH-CO-NH-R^1$$

wherein $R^1$ is as aforesaid, is heated at a temperature of from 150° to 280° C. and under a pressure of from 50 mbar to 5 bars in the presence of N-methyl pyrrolidone or sulfolan as solvent, said reaction being accompanied by the elimination of ammonia.

3. A process according to claim 1, wherein the reaction is effected in the presence of an acid or basic catalyst.

4. A process according to claim 1, wherein the temperature is in the range from 175° to 220° C.

* * * * *